United States Patent [19]

Wecker et al.

[11] Patent Number: 5,098,262

[45] Date of Patent: Mar. 24, 1992

[54] SOLUTION PUMPING SYSTEM WITH COMPRESSIBLE PUMP CASSETTE

[75] Inventors: Sheldon M. Wecker; Kent D. Abrahamson; Thomas P. Joyce, all of Libertyville, Ill.

[73] Assignee: Abbott Laboratories, Abbott Park, Ill.

[21] Appl. No.: 635,906

[22] Filed: Dec. 28, 1990

[51] Int. Cl.⁵ .............................................. F04B 43/12
[52] U.S. Cl. .................................... 417/479; 604/153
[58] Field of Search ................ 417/474, 479, 413; 604/153

[56] References Cited

U.S. PATENT DOCUMENTS

| | | | |
|---|---|---|---|
| 4,303,376 | 12/1981 | Siekmann | 417/479 X |
| 4,411,603 | 10/1983 | Kell | 417/479 |
| 4,758,238 | 7/1988 | Sundblom et al. | 604/153 X |
| 4,818,186 | 4/1989 | Pastrone et al. | 417/413 |

Primary Examiner—Leonard E. Smith
Attorney, Agent, or Firm—A. Nicholas Trausch

[57] ABSTRACT

A solution pumping system includes a compressible pump cassette having front and rear body members, and an elastomeric diaphragm positioned therebetween. The front and rear body members are joined to each other for limited, relative movement, which movement effects compression of the diaphragm. The pump cassette is removably positionable in a pump driver of the system, which can be configured to effect compression of the cassette for use. In this way, the desired compression of the diaphragm during use can be achieved, while avoiding problems associated with compression set or load decay during storage of the cassette prior to use.

15 Claims, 3 Drawing Sheets

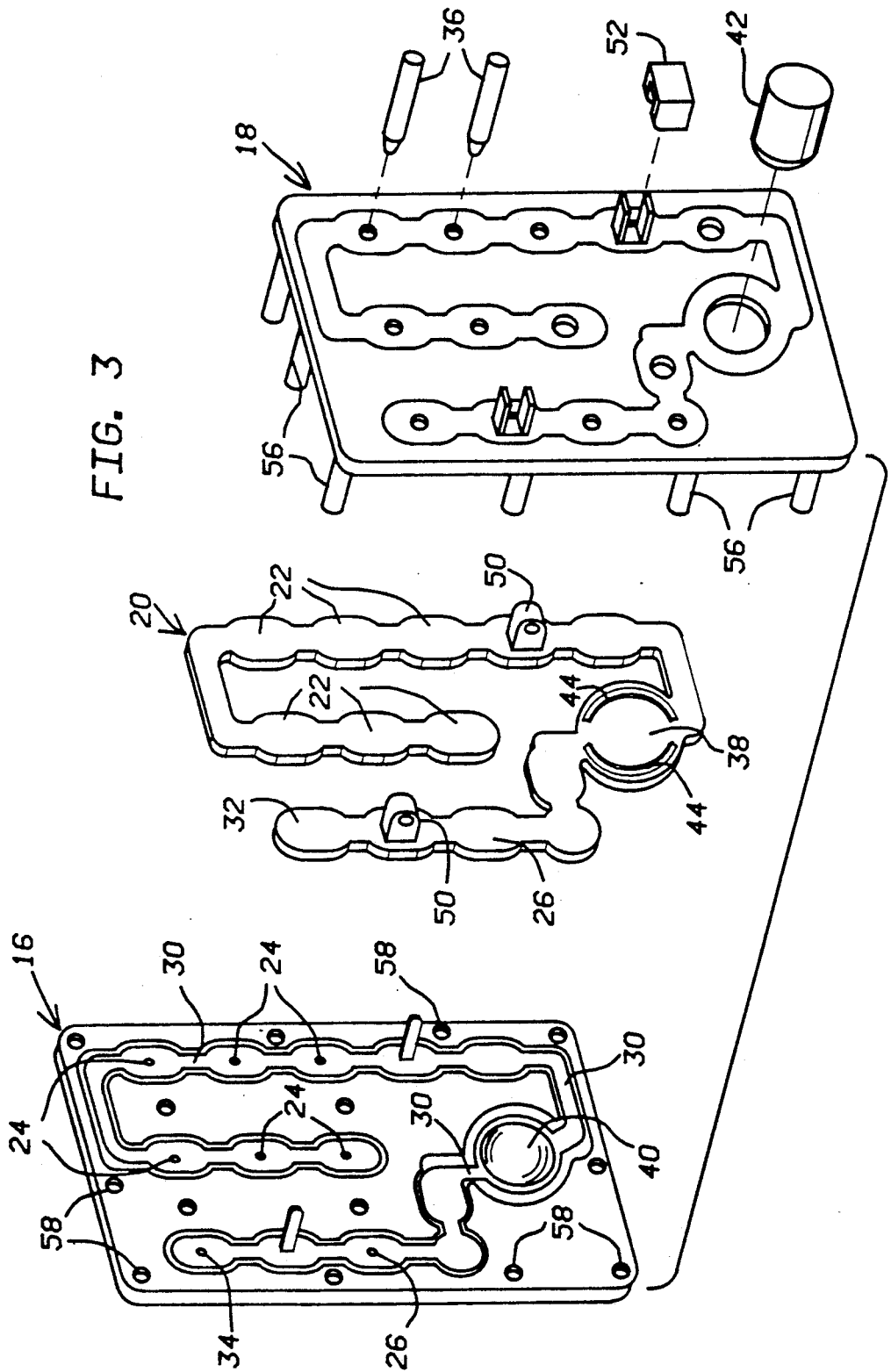

SOLUTION PUMPING SYSTEM WITH COMPRESSIBLE PUMP CASSETTE

TECHNICAL FIELD

The present invention relates generally to solution pumping systems for preparation and administration of patient parenteral solutions, and more particularly to a solution pumping system including a disposable pump cassette having a cassette body configured for effecting compression of an internal diaphragm of the cassette attendant to use, thereby avoiding undesirable compression set of the diaphragm material during storage prior to use.

BACKGROUND OF THE INVENTION

Modern health care facilities require preparation and administration of very large numbers of parenteral solutions to patients. Such solutions include those administered for both nutritional and therapeutic purposes.

In recent years, positive displacement fluid infusion pumping devices have been developed for administration of parenteral solutions to patients. Such infusion pumping devices permit precise control of drug administration to a patient during a given period of time, and facilitate efficient and accurate solution administration.

U.S. Pat. No. 4,639,245, to Pastrone et. al., U.S. Pat. No. 4,88,186, to Pastrone et.al., and U.S. Pat. No. 4,842,584, to Pastrone, all of which are hereby incorporated by reference, disclose a positive displacement fluid infusion pumping device and components thereof, which have met with widespread acceptance by the health care industry. This pumping system includes a combination of a pump driver and an associated removable and disposable pump cassette. The pump cassette includes a self-contained positive displacement pump device, which is operated by a reciprocable pump plunger of the associated pump driver. The pump driver further includes selectively operable valve actuators, which cooperate with valve mechanisms provided in the pump cassette for accurate and highly automated administration and infusion of parenteral solutions.

Pending U.S. application Ser. No. 07/444,459, filed Dec. 1, 1989, discloses a solution pumping system generally of the above type, including a disposable pump cassette, and associated pump driver. The system of this pending application is particularly configured for automated compounding and preparation of parenteral solutions, for subsequent infusion to a patient. Portions of the above-identified application, not inconsistent with the present disclosure, are hereby incorporated by reference.

Solution pumping systems of the above infusion and compounding types employ preassembled, disposable pump cassettes. Such pump cassettes typically include a cassette body including juxtaposed front and rear body members, between which is positioned a membrane-like elastomeric diaphragm. The diaphragm cooperates with the front body member to provide valve mechanisms at various inlets and outlets defined by the front body member, with openings in the rear body member exposing the diaphragm for operation of the valve mechanisms by valve actuators of the associated pump driver.

Additionally, the front body member of the cassette defines a pump chamber which, together with the internal diaphragm, provides the self-contained positive displacement pump of the cassette. The rear body member defines an opening through which a reciprocable plunger of the associated pump driver is movable for operating the pump, whereby liquid can be pumped through the cassette.

As will be appreciated, the accurate and consistent pumping of liquids requires that during use, the various components of the cassette, including the internal diaphragm, remain in secure association with each other. This is particularly true in the region of the diaphragm which provides the pump mechanism, since this portion of the diaphragm is repeatedly deformed by the associated reciprocable pump plunger.

In the past, the components of such disposable cassettes have been subjected to compression during assembly, whereby the front and rear body portions of the cassette act to grip the internal diaphragm to retain it in the desired position and orientation. The components are then permanently joined together, such as by sonic welding of the body members, with the diaphragm thus retained in compression.

However, experience has shown that some constructions do not lend themselves to creating sufficient compression of the diaphragm attendant to sonic welding or other joining of the body members together. Additionally, this compression of the diaphragm can lead to "compression set" or "load decay", a cold-flow or creep-like phenomenon which can be exhibited by the elastomeric diaphragm material during storage of the cassette prior to use. As a consequence of this compression set, the initial degree of compression created on the diaphragm during cassette assembly can undesirably be lost.

The present invention contemplates avoiding the problems of compression set or load decay by assembling a pump cassette under relatively low compression, with the cassette being subjected to compression attendant to use so that high pumping pressures can desirably be achieved.

SUMMARY OF THE INVENTION

A solution pumping system embodying the principles of the present invention includes a pump driver, and a compressible pump cassette having a body formed from front and rear members which are relatively movable under the influence of a compression mechanism, which can be provided in the pump driver, or which may comprise a separate fixture fitted to the cassette before insertion of the cassette into the driver. By this arrangement, an internal elastomeric diaphragm of the cassette is subjected to relatively high compression only during use of the cassette, thus avoiding deformation of the diaphragm by compression set or load decay during storage of the cassette prior to use.

The pump cassette of the present system is configured for use with a pump driver having a reciprocable pump plunger, and a plurality of valve actuators. The cassette includes a cassette body having a generally plate-like front body member, and a juxtaposed, generally plate-like rear body member.

The cassette further includes a membrane-like elastomeric diaphragm positioned in the cassette body between the front and rear body members. The cassette body and the diaphragm cooperate to provide the cassette with at least one liquid inlet, at least one liquid outlet, and a liquid flow path for joining the liquid inlet and outlet in fluid communication with each other. The cassette further includes a positive displacement pump operatively driven by the pump plunger of the associated pump driver for pumping liquid from the inlet to the outlet via the flow path defined by the cassette.

In accordance with the present invention, the front and rear body members of the cassette body are non-rigidly joined to each other for limited, relative movement toward each other for effecting compression of the elastomeric diaphragm when the pump cassette is operatively associated with the pump driver. During such relatively limited movement, the generally plate-like front and rear body members are maintained in substantially parallel relationship to each other, with the internal diaphragm compressed therebetween.

To provide the desired limited, relative movement of the front and rear body members of the cassette, the illustrated embodiment includes a plurality of fastening elements in the form of rivets. Each rivet includes a shank portion and a head portion, with at least one of the front and rear body portions being movable along the shank portions of the rivets for providing the desired relative movement of the body portions. The head portions, in turn, act to maintain the front and rear body portions in juxtaposition to each other, with preferably relatively low compression of the internal diaphragm, such as during storage prior to use. As will be appreciated, fastening elements other than rivets can be employed for movably joining the body members.

While it is contemplated that the body members can be joined by separately provided rivets or other like fastening elements, the illustrated embodiment of the present invention includes rivets integral with one of the body members, specifically the rear body member, with the other of the body members movable along the shank portions of the rivets.

The pump driver of the present system is particularly configured to effect compression of the cassette body when the pump cassette is removably positioned in the driver, thereby effecting the desired limited, relative movement of the front and rear body members of the cassette for compressing the internal diaphragm thereof. In the illustrated embodiment, the pump driver includes a reciprocably movable cassette door which is movable toward and away from a cassette-receiving faceplate of the driver.

The pump cassette is removably positionable between the cassette door and the faceplate, whereby movement of the door toward the faceplate acts to compress the cassette body. In the illustrated embodiment, the cassette door defines clearance openings in the regions of each of the rivets of the cassette for providing clearance for the head portions of the rivets during compression of the cassette body by the pump driver.

While the illustrated embodiment provides the desired compression-effecting mechanism in the pump driver cassette door, a separately provided fixture, functioning in the nature of a clip or clamp, can alternately be employed to permit the cassette to be compressed externally of the driver. Such a fixture can be configured for securement to the cassette prior to disposition of the cassette in operative association with the pump driver, whereby the desired compression is maintained during use.

Other features and advantages of the present invention will become readily apparent from the following detailed description, the accompanying drawings, and the appended claims.

BRIEF DESCRIPTION OF THE DRAWINGS

FIG. 3 is an exploded perspective view of a disposable pump cassette of the present system illustrated, in diagrammatic form, in operative association with the pump driver of the present system;

DETAILED DESCRIPTION

Figure 1:
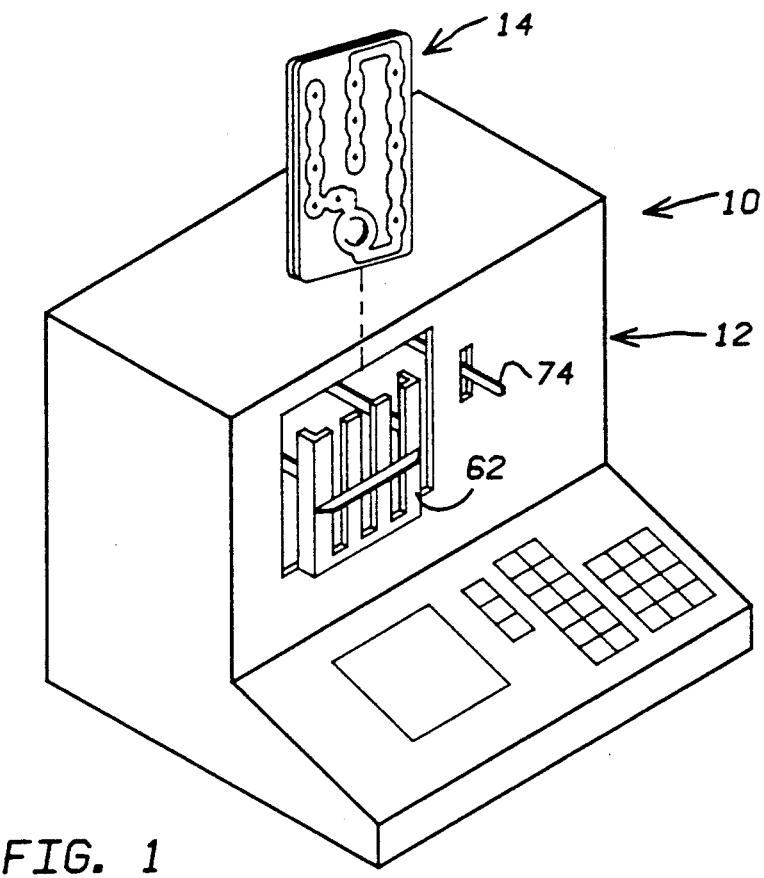
FIG. 1 is a diagrammatic perspective view of a solution pumping system, embodied as a compounding system for parenteral solutions, embodying the principles of the present invention.

While the present invention is susceptible of embodiment in various forms, there is shown in the drawings and will hereinafter be described a presently preferred embodiment of the invention, with the understanding that the present disclosure is to be considered as an exemplification of the invention, and is not intended to limit the invention to the specific embodiment illustrated.

With reference now to the drawings, therein is illustrated a solution pumping system 10 embodying the principles of the present invention. In the illustrated embodiment, the present system has been particularly configured for compounding of parenteral admixture solutions for intravenous or intramuscular administration to patients. However, as will be appreciated, a solution pumping system embodying the principles of the present invention can be used for other applications, including infusion of parenteral solutions.

The solution pumping system 10 of the present invention includes a pump driver 12 and an associated disposable pump cassette 14 which is removably positionable in the pump driver 12. As will be further discussed, the pump cassette 14 is of a compressible or collapsible nature, with the pump driver 12 of the illustrated embodiment configured for effecting compression of the pump cassette when it is positioned within the pump driver for use. During use, the pump cassette is typically associated with a disposable "set" of suitable tubing and connectors, which set is joined to containers of various source solutions. The resultant solution admixtures are introduced into suitable storage containers joined to the tubing set.

Referring particularly to FIG. 3, the configuration of the pump cassette 14 will first be described. In the preferred embodiment, the pump cassette comprises a generally rectangular cassette body which comprises a front body member 16 and a juxtaposed rear body member 18. The cassette body is preferably formed from rigid thermoplastic material, such as polycarbonate.

The pump cassette further includes a deformable elastomeric diaphragm 20 positioned between the front and rear body portion. Diaphragm 20 cooperates with the cassette body, and in particular with the front body member 16, to define and provide at least one liquid inlet, at least one liquid outlet, and a liquid flow path joining the inlet and outlet in fluid communication. The diaphragm cooperates with the front body member 16 to provide a selectively operable valve mechanism at each of the various liquid inlets and outlets.

Specifically, the diaphragm 20 includes a plurality of inlet portions 22 respectively positioned in association with a plurality of liquid inlets 24 defined by front body member 16. Similarly, the diaphragm includes an outlet portion 26 which cooperates with a liquid outlet 28 defined by front body member 16. The diaphragm 20 and the front body member 16 together define a liquid flow path 30 which joins the liquid inlets and the outlet in fluid communication with each other. In the illustrated form, the diaphragm 20 includes a flush portion 32 arranged in confronting, cooperating relationship with a flush port 34 defined by the front body member 16, which port facilitates flushing of the cassette and associated tubing during admixture of solutions.

The various portions of the diaphragm 20 cooperate with the front body portion to provide a plurality of valve mechanisms, each operated by deformation and relaxation of the diaphragm 20. To this end, the rear body member 18 defines a plurality of openings respectively aligned with the portions of the diaphragm which cooperate with the front body member to provide the valve mechanisms. The pump driver 12 of the system includes a plurality of valve actuators 36 (two being diagrammatically illustrated in FIG. 3) which are configured to extend through the openings in the rear body member 18 and contact the diaphragm for effecting the desired selective opening and closing of the inlets and outlets of the pump cassette.

Each of the valve actuators preferably comprises a solenoid-actuated arrangement for reciprocating the actuator, thereby controlling liquid flow through the respective inlet or outlet. In a particularly preferred embodiment, as disclosed in copending U.S. Pat. application Ser. No. 07/444,477, filed Dec. 1, 1989, a solenoid-operated valve actuator is employed, which actuator is configured to provide the desired closing force while avoiding excessive stress of the diaphragm 20. It is preferred that the solenoid of the valve actuator employed in the present system be configured for closing (under the influence of a return spring) in the event of power failure.

In order to effect pumping of liquids, the pump cassette 14 includes a self-contained positive displacement pump mechanism. Specifically, the diaphragm 20 defines a generally circular pump portion 38, which is positioned in operative association with a pump chamber 40 defined by front body member 16. Operation of the pump mechanism, by deformation and relaxation of the pump portion 38, is effected by a reciprocable pump plunger 42 of the pump driver. Operation of the pump can be in accordance with U.S. Pat. No. 4,639,245, to Pastrone et.al. Essentially, liquid flow is effected by reciprocation of the pump plunger 42 in timed relation to operation of selected ones of the valve actuators upstream and downstream of the pump chamber. A reversible stepping motor, acting through a suitable threaded connection, provides reciprocable stroking of the pump plunger for alternately deforming and relaxing the diaphragm portion 38, thus effecting positive displacement of liquid in the pump chamber 40.

As will be further described, the front and rear body members 16 and 18 of the cassette are movable toward each other for effecting compression of the diaphragm 20, to thereby securely grip and retain the diaphragm in position during pumping, as well as during operation of the various valve mechanisms. In the preferred form, the diaphragm 20 includes a relatively enlarged bead portion 44 surrounding the pump portion 38, which bead portion 44 cooperates with a pair of first clamping ribs 46 and a pair of second clamping ribs 48, respectively positioned on the front and rear body members 16 and 18 about the pump chamber. The first and second clamping ribs are engageable with the diaphragm on respective opposite sides thereof, with the bead portion 44 held and gripped therebetween. Attendant to limited relative movement of the front and rear body members, the first and second clamping ribs are relatively movable toward each other for effecting compression of the diaphragm 20.

Various other features can be provided in the pump cassette 4 if desired. For example, the diaphragm 20 can be configured to include air detection portions 50 which project rearwardly through rear body member 18 so that a portion of the liquid flow path extends rearwardly from the rear body member. Each of the air detection portions 50 is received within a respective air detector 52 (one being illustrated in FIG. 3). The diaphragm 20 is preferably formed from a translucent, silicone-based elastomer, with the air detector 52 preferably configured to ultrasonically or optically detect the presence of air, and thus the absence of liquid, in the respective portion 50.

In accordance with the present invention, the front and rear body members 16 and 18 are joined to each other for limited, relative movement. To this end, the cassette includes a plurality of rivets 56 or like fastening members which are each configured to extend within respective openings 58 for staking the body members to each other. While the rivets can be separately provided, it is presently preferred that the rivets 56 be integral with either one of the body portions (integral with rear body portion 18 in the illustrated embodiment), with the other of the body members (front body member 16 in the illustrated form), being movable along the shank portions of the rivets 56. Each of the rivets 56 also includes a deformed head portion, with the head portions collectively retaining the body members together after assembly of the cassette. The rivets are preferably configured for heat-deformation (such as by ultrasonic staking), and thus may be of a generally hollow configuration, as illustrated, to facilitate such heat-deformation subsequent to juxtaposition of the body members with the diaphragm 20 therebetween.

As discussed above, it is contemplated that the cassette 14 be assembled with relatively low compression of the various components, and thus relatively low stress, to avoid problems associated with compression set or load decay during storage prior to use. By way of example, the diaphragm 20 can be compressed on the order of about 0.005 inches during assembly, with the head portions of the rivets 56 deformed to maintain the assembly in this configuration. Subsequent compression of the cassette 14 by the pump driver 12 acts to relatively move the body members, with the front body member 16 moving along the shank portions of the rivets 56 for effecting the desired degree of compression of the diaphragm 20 for high-pressure operation.

If desired, the cassette 14 can optionally be configured to include one or more positive stop elements or the like for limiting the relative movement of the front and rear body members 16 and 18, thereby limiting the compression of the elastomeric diaphragm 20. Such an arrangement can take the form of one or more stop flanges 59, such as shown in phantom line in FIGS. 5 and 6, integral with one of the front and rear body members (the rear body member 18 in the illustrated form). Alternatively, the rivets 56 joining the body members can similarly be provided with such a travel-limiting arrangement. This construction acts to limit the extent of diaphragm compression to a preselected value, and is believed to desirably reduce tolerance stack-up during manufacture and assembly.

Figure 2:
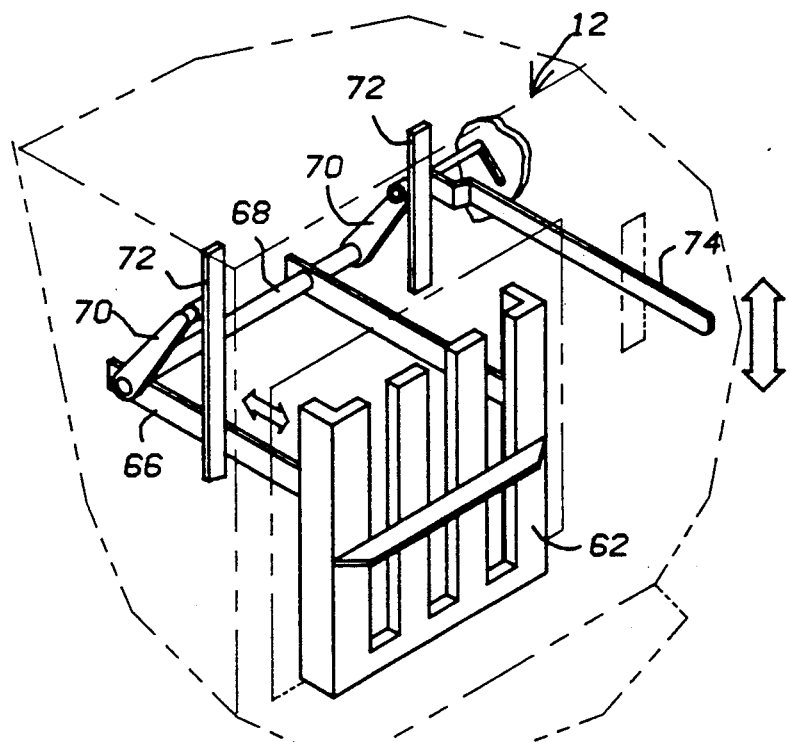
FIG. 2 is a diagrammatic view illustrating a cassette-receiving door mechanism of a pump driver of the present system.

With reference now to FIG. 2, the cassette-receiving door mechanism of the pump driver 12 is diagrammatically illustrated. In particular, the mechanism includes a reciprocable cassette door 62 generally within which the cassette 14 is removably positionable. The cassette door 62 is movable generally inwardly and outwardly relative to a faceplate 64 (not shown in FIG. 3; see FIGS. 5 and 6) for effecting compression of the pump cassette 14 therebetween.

While it is presently contemplated that compression of the cassette 14 be effected by the action of the door 62, the desired compression can alternately be provided, externally of the pump driver 12, such as by the provision of a separate clamp-like or clip-like fixture fitted to the cassette. Such a fixture, diagrammatically illustrated at 61 in FIG. 6, can be fitted to the cassette prior to its positioning in association with the pump driver 12, thereby maintaining the cassette in compression during use.

Although the specific configuration of the cassette-receiving door mechanism can be varied in accordance with the teachings disclosed herein, the illustrated embodiment includes a pair of support arms 66 on which the reciprocable cassette door 62 is mounted, with the arms 66 in turn mounted on a shaft 68. A pair of cams 70 are joined to the shaft 68, with the cams 70 being configured for cooperative reaction against a pair of fixed end beam springs 72 attendant to vertical movement of operating lever 74. By this arrangement, upward movement of the lever 74 acts to open the door 62 for insertion and removal of the pump cassette 14, with downward movement of the lever 74 acting to urge the door toward the facing plate 64, thereby compressing the cassette 14 between the door and the faceplate.

Figure 6:
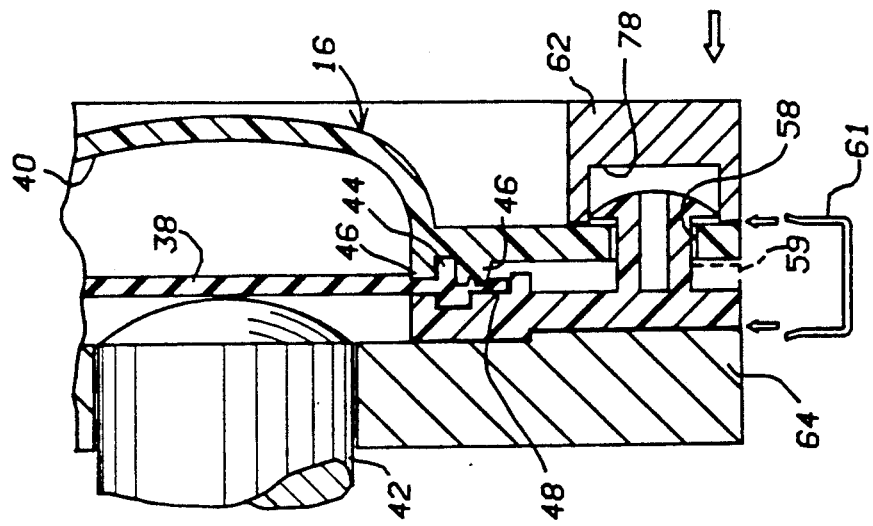
FIG. 6 is a view similar to FIG. 5 illustrating compression of the pump cassette.
Figure 5:
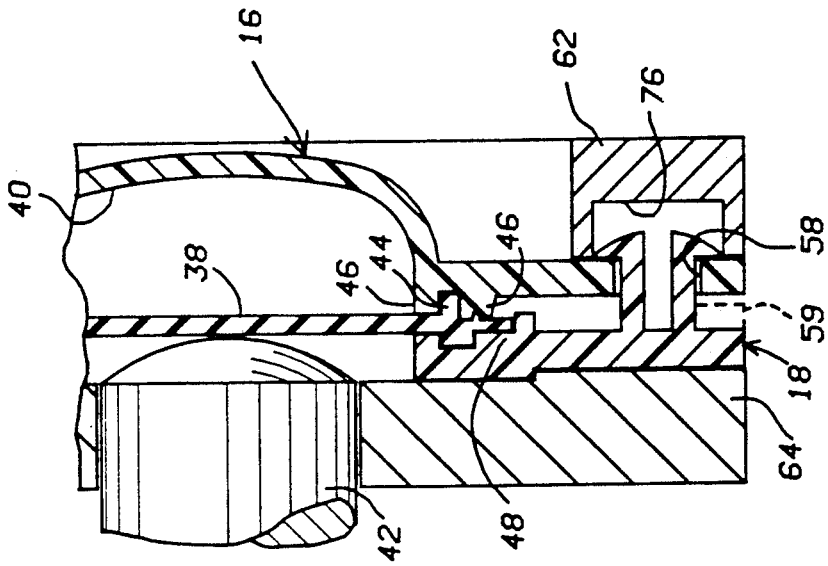
FIG. 5 is a fragmentary, cross-sectional view taken along lines 5—5 of FIG. 4.
Figure 4:
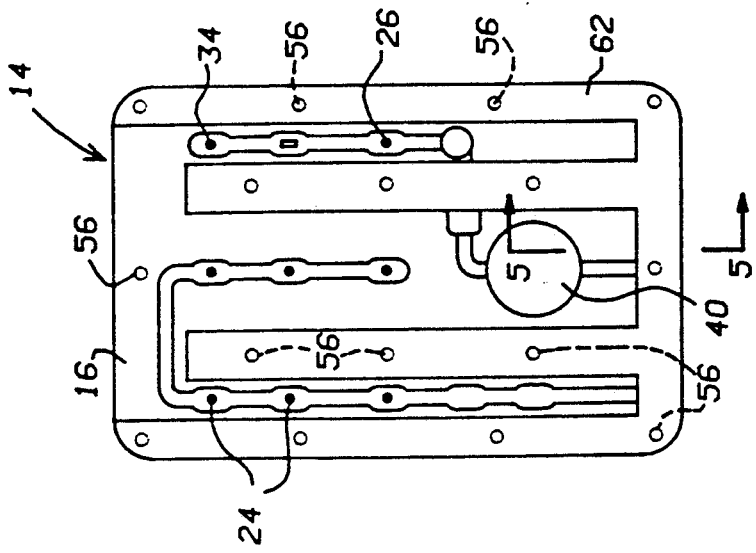
FIG. 4 is a front, elevational diagrammatic view of the pump cassette of the present system in position within the cassette door or the associated pump driver.

FIGS. 5 and 6 illustrate compression of the cassette 14, including relative movement of the front and rear body members 16 and 18 for compression of diaphragm 20. The degree of compression is selected to permit operation of the pump cassette at the desired high pressures without any leakage of liquid from the flow path 30, or the pump chamber 40. As illustrated in FIGS. 5 and 6, the door 62, which acts to effect compression of the pump cassette 14, preferably defines clearance openings 76 (one being illustrated) for providing clearance for the head portions of the rivets 56 during compression of the cassette body by the door mechanism of the pump driver 12.

From the foregoing, it will be observed that numerous modifications and variations can be effected without departing from the true spirit and scope of the novel concept of the present invention. It is to be understood that no limitation with respect to the specific embodiment illustrated is intended or should be inferred. The disclosure is intended to cover by the appended claims all such modifications as fall within the scope of the claims.

What is claimed is:

1. A pump cassette for use with an associated pump driver having a reciprocable pump plunger and a plurality of valve actuators, said pump cassette comprising:

a cassette body comprising a front body member, and a juxtaposed rear body member; and elastomeric diaphragm means positioned in said cassette body between said front and rear body members, said cassette body and said diaphragm means together providing said pump cassette with at least one liquid inlet, at least one liquid outlet, a liquid flow path for joining said liquid inlet and outlet in fluid communication, and pump means operably driven by the pump plunger of said associated pump driver for pumping liquid from said inlet to said outlet via said flow path, said front and rear body members of said cassette body being joined to each other for limited, relative movement toward each other for effecting compression of said elastomeric diaphragm means when said pump cassette is operably associated with said pump driver.

2. A pump cassette in accordance with claim 1, wherein each of said front and rear body members has a generally plate-like configuration, said body members being maintained in substantially parallel relationship to each other during said relative movement of said body members.

3. A pump cassette in accordance with claim 1, wherein said front body member defines a pump chamber which cooperates with said elastomeric diaphragm means to provide said pump means, said front body member further defining first clamping rib means positioned about said pump chamber for engagement with said diaphragm means said rear body member defining second clamping ribs engageable with said diaphragm means in cooperation with said first clamping rib means defined by said front body means for gripping said diaphragm means, said first and second clamping rib means being relatively movable toward each other during said relative movement of said front and rear body members for effecting compression of said diaphragm means.

4. A pump cassette in accordance with claim 1, wherein said front and rear body members are joined to each other with a plurality of fastening means each having a shank portion and a head portion, at least one of said front and rear body portions being movable along the shank portions of said fastening means for providing said relative movement of said body portions, said head portions of said fastening means maintaining said front and rear body portions in juxtaposition to each other.

5. A pump cassette in accordance with claim 4, wherein said plurality of fastening means are integral with one of said front and rear body portions, the other of said body portions being movable along the shank portions of said fastening means.

6. A pump cassette in accordance with claim 1, including stop means for limiting the relative movement of said front and rear body members for limiting the compression of said elastomeric diaphragm means.

7. A pump cassette in accordance with claim 6, wherein
said stop means comprises stop flange means integral with one of said front and rear body members.

8. A pump cassette in accordance with claim 1, including
means for maintaining compression of said cassette externally of said pump driver.

9. A solution pumping system, comprising:
a pump driver, including reciprocable pump plunger, and a plurality of valve actuators; and
a pump cassette removably positionable in operative association with said pump driver,
said pump cassette including a cassette body comprising a front body member and a juxtaposed rear body member, and an elastomeric diaphragm positioned between said front and rear body member,
said front body member defining together with said diaphragm at least one liquid inlet, at least one liquid outlet, a liquid flow path for joining said inlet and outlet in fluid communication, and pump means operably driven by the pump plunger of said associated pump driver for pumping liquid from said inlet to said outlet via second flow path when said cassette is positioned in said pump driver,
said front and rear portions of said cassette body being joined to each other for limited relative movement toward each other for effecting compression of said elastomeric diaphragm.

10. A solution pumping system in accordance with claim 9, wherein
said pump driver includes means for compressing said cassette body for relative movement of said front and rear body members when said cassette is positioned in said pump driver.

11. A solution pumping system in accordance with claim 10, wherein
said compressing means includes a reciprocably movable cassette door movable toward and away from a faceplate of the pump driver, said pump cassette being movably positionable between said cassette door and said faceplate, and said door movable toward said faceplate for compressing said cassette body.

12. A solution pumping system in accordance with claim 9, wherein
said front and rear body members of said cassette body are joined to each with a plurality of fastening means each having a shank portion and a head portion, at least one said front and rear body portion being movable along the shank portions of said fastening means for providing said relative movement of said body portions, said head portions of said fastening means maintaining said front and rear body portions in juxtaposition to each other.

13. A solution pumping system in accordance with claim 12, wherein
said pump driver includes means for providing clearance for said head portions of said fastening means during compression of said cassette body.

14. A solution pumping system in accordance with claim 9, wherein
said pump cassette includes stop means for limiting the relative movement of said front and rear body members for limiting the compression of said elastomeric diaphragm means.

15. A solution pumping system in accordance with claim 9, including
fixture means which can be fitted to said cassette prior to its positioning in association with said pump driver for maintaining the cassette in compression during use.

* * * * *